United States Patent
Ohno et al.

(10) Patent No.: US 10,561,306 B2
(45) Date of Patent: Feb. 18, 2020

(54) ENDOSCOPIC DEVICE

(71) Applicants: Sony Olympus Medical Solutions Inc., Tokyo (JP); Sony Corporation, Tokyo (JP)

(72) Inventors: Naoyuki Ohno, Tokyo (JP); Masahiro Kojima, Aichi (JP); Shigeru Teshigahara, Gifu (JP)

(73) Assignees: SONY OLYMPUS MEDICAL SOLUTIONS INC., Tokyo (JP); SONY CORPORATION, Tokyo (JP)

(*) Notice: Subject to any disclaimer, the term of this patent is extended or adjusted under 35 U.S.C. 154(b) by 335 days.

(21) Appl. No.: 15/356,811

(22) Filed: Nov. 21, 2016

(65) Prior Publication Data
US 2017/0172388 A1    Jun. 22, 2017

(30) Foreign Application Priority Data
Dec. 21, 2015   (JP) .................. 2015-248860

(51) Int. Cl.
| A61B 1/05 | (2006.01) |
| A61B 1/00 | (2006.01) |
| H04N 5/225 | (2006.01) |
| A61B 1/04 | (2006.01) |

(52) U.S. Cl.
CPC .......... *A61B 1/051* (2013.01); *A61B 1/00124* (2013.01); *A61B 1/00126* (2013.01); *A61B 1/042* (2013.01); *A61B 1/05* (2013.01); *A61B 1/053* (2013.01); *H04N 5/2253* (2013.01); *H05K 2201/10378* (2013.01)

(58) Field of Classification Search
CPC ....... A61B 1/00124; A61B 1/05; A61B 1/051; H05K 2201/10378
See application file for complete search history.

(56) References Cited

U.S. PATENT DOCUMENTS

| 4,604,519 A | * | 8/1986 | Zollman | ............... H01J 29/026 250/214 VT |
| 5,258,648 A | * | 11/1993 | Lin | .................... G01R 31/2863 257/747 |
| 5,474,458 A | * | 12/1995 | Vafi | .................... H01L 23/49827 257/E23.063 |
| 6,740,811 B2 | | 5/2004 | Kurita | |
| 7,582,973 B2 | | 9/2009 | Hamaguchi | |

(Continued)

FOREIGN PATENT DOCUMENTS

| JP | 2002-176069 A | 6/2002 |
| JP | 2007-012896 A | 1/2007 |

(Continued)

OTHER PUBLICATIONS

Japanese Office Action dated Sep. 10, 2019, issued in corresponding Japanese Patent Application No. 2015-248860, 13 pages. (with English translation).

*Primary Examiner* — Aaron B Fairchild
(74) *Attorney, Agent, or Firm* — Xsensus LLP

(57) ABSTRACT

There is provided an endoscopic device, including: an image sensor section including an image sensor that senses and converts lights into an electrical signal; a substrate that is electrically connected to the image sensor section; and an intermediate unit, interposed between the image sensor section and the substrate, that electrically connects the image sensor section and the substrate.

3 Claims, 8 Drawing Sheets

(56) References Cited

U.S. PATENT DOCUMENTS

| | | | |
|---|---|---|---|
| 7,785,024 B2 | 8/2010 | Fujimori | |
| 2002/0185717 A1* | 12/2002 | Eghan | H01L 23/055 257/678 |
| 2007/0019952 A1* | 1/2007 | Fujimori | G03B 17/02 396/529 |
| 2012/0327574 A1 | 12/2012 | Sakaguchi et al. | |

FOREIGN PATENT DOCUMENTS

| | | |
|---|---|---|
| JP | 2007-109790 A | 4/2007 |
| JP | 2011-346 | 1/2011 |
| JP | 2011-66093 A | 3/2011 |
| JP | 2013-021085 A | 1/2013 |
| JP | 2013-30748 A | 2/2013 |
| JP | 2014-187389 A | 10/2014 |
| WO | 2007/013214 A1 | 2/2007 |

\* cited by examiner

ENDOSCOPIC DEVICE

CROSS REFERENCE TO RELATED APPLICATIONS

This application claims the benefit of Japanese Priority Patent Application JP 2015-248860 filed Dec. 21, 2015, the entire contents of which are incorporated herein by reference.

BACKGROUND

The present disclosure relates to an endoscopic device.

Heretofore, in the medical field, there are known endoscopic devices that use an image sensor to image the interior (the inside of the body) of a target of observation, such as a person, and enable observation of the inside of the body (see JP 2011-000346A, for example). The endoscopic device described in JP 2011-000346A is equipped with an image sensor that captures a subject image in which light has been condensed by an insertion section inserted inside the body, and a drive circuit board for driving the image sensor. In the endoscopic device, the relative positions of the image sensor and the drive circuit board are fixed by a spacer.

SUMMARY

Meanwhile, in some cases, the endoscopic device disclosed by JP 2011-000346A may be exposed to high temperature (120° C., for example) by a sterilization process, such as with an autoclave. In such cases, since components such as the image sensor, the drive circuit board, and the spacer provided in the endoscopic device are exposed to high temperature, each of these components undergoes thermal expansion. However, in JP 2011-000346A, this thermal expansion is not considered, and because of the respective stresses imparted to the joint interfaces with the spacer due to differences in the individual coefficients of thermal expansion, there is a risk of a faulty electrical connection occurring between the image sensor and the drive circuit board.

The present disclosure has been devised in light of the above, and provides an endoscopic device capable of making a reliable electrical connection between an image sensor and a substrate, even when exposed to high temperature.

According to an embodiment of the present disclosure, there is provided an endoscopic device, including: an image sensor section including an image sensor that senses and converts lights into an electrical signal; a substrate that is electrically connected to the image sensor section; and an intermediate unit, interposed between the image sensor section and the substrate, that electrically connects the image sensor section and the substrate.

The intermediate unit may include an intermediate member formed using a material having a coefficient of thermal expansion that is the same as a coefficient of thermal expansion of the image sensor section, or a coefficient of thermal expansion that is close to the coefficient of thermal expansion of the image sensor section from between the image sensor section and the substrate.

The intermediate unit may additionally include solder balls that electrically connect the intermediate member and the substrate, and underfill, provided between the intermediate member and the substrate, that secures the intermediate member and the substrate.

The endoscopic device may further include: solder balls that electrically connect the image sensor section and the intermediate member.

The intermediate unit may include an electrically conductive, elastically deformable elastic member provided between the image sensor section and the substrate.

The intermediate unit may include an intermediate member formed using a material having a coefficient of thermal expansion that is the same as a coefficient of thermal expansion of the image sensor section, or a coefficient of thermal expansion that is close to the coefficient of thermal expansion of the image sensor section from between the image sensor section and the substrate, and an electrically conductive elastic member, provided between the intermediate member and the substrate, that retractably connects the intermediate member and the substrate from one to the other.

According to an embodiment of the present disclosure, there is exhibited an advantageous effect of making a reliable electrical connection between an image sensor and a substrate, even when exposed to high temperature.

DETAILED DESCRIPTION OF THE EMBODIMENT(S)

Hereinafter, embodiments for carrying out the present disclosure (hereinafter designated the exemplary embodiments) will be described. In the embodiments, an endoscopic device for medical use that captures and displays an interior image of a test subject such as a patient will be described as an example of a medical image acquisition system including a medical imaging device according to an embodiment of the present disclosure. In addition, the present disclosure is not limited by these embodiments. Furthermore, in the description of the drawings, like portions are denoted by like signs.

(Embodiment 1)

Figure 1:
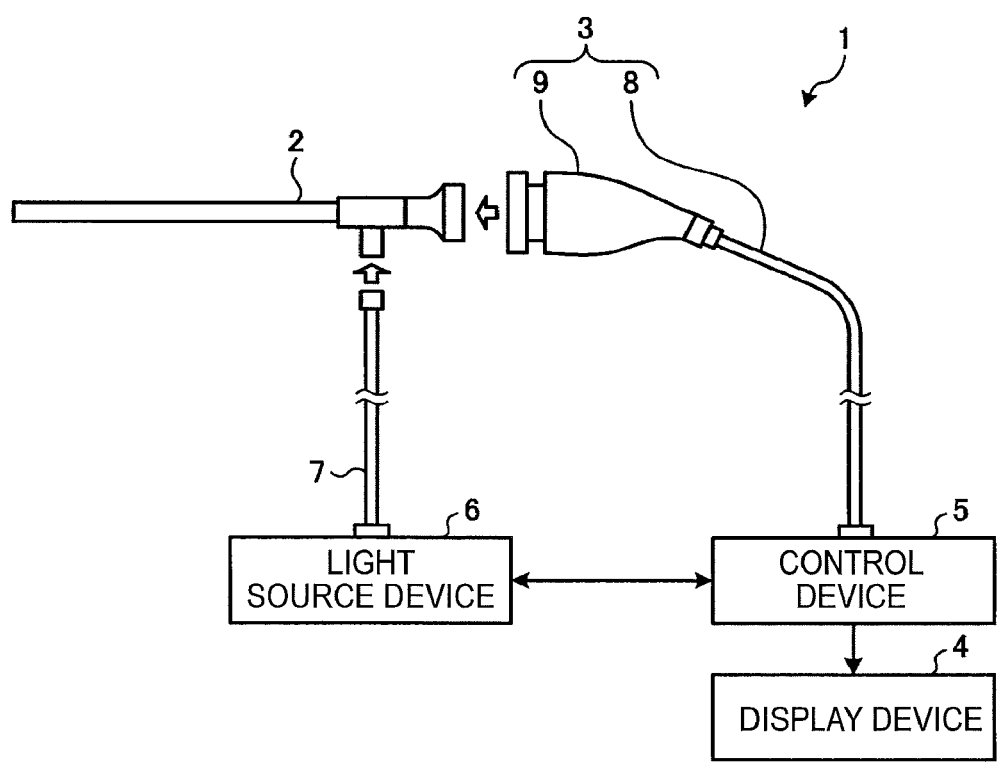
FIG. 1 is a diagram illustrating a schematic configuration of an endoscopic device according to Embodiment 1 of the present disclosure.

FIG. 1 is a diagram illustrating a schematic configuration of an endoscopic device 1 according to Embodiment 1 of the present disclosure. The endoscopic device 1 is a device used in the medical field that enables one to observe a photographic subject of the interior (the inside of the body) of a target of observation, such as a person. As illustrated in FIG. 1, the endoscopic device 1 is equipped with an endoscope 2, an imaging device 3, a display device 4, a control device 5, and a light source device 6.

One end of a light guide 7 is connected to the endoscope 2, and the light source device 6 supplies white illuminating light for illuminating the inside of the body to the one end of the light guide 7. One end of the light guide 7 is removably connected to the light source device 6, while the other end is removably connected to the endoscope 2. Additionally, the light guide 7 transmits light supplied from the light source device 6 from the one end to the other end, thereby supplying the light to the endoscope 2.

The imaging device 3 captures a subject image from the endoscope 2, and outputs the imaging result. As illustrated in FIG. 1, the imaging device 3 is equipped with a transmission cable 8 which acts as a signal transmission section, and a camera head 9. In Embodiment 1, the medical imaging device is constituted by the transmission cable 8 and the camera head 9.

The endoscope 2 has a rigid, long and narrow shape, and is inserted inside the body. Provided in the interior of the endoscope 2 is an optical system, which is made up of one or multiple lenses, and which condenses the light of the subject image. The endoscope 2 emits light supplied through the light guide 7 from the leading end, and irradiates the inside of the body. Additionally, the light radiated inside the body (that is, the subject image) is condensed by the optical system (lens unit 91) inside the endoscope 2.

The camera head 9 is removably connected to the base end of the endoscope 2. Additionally, the camera head 9, under control by the control device 5, captures a subject image condensed by the endoscope 2, and outputs an imaging signal according to the imaging. Note that the detailed configuration of the camera head 9 will be discussed later.

One end of the transmission cable 8 is removably connected to the control device 5 through a connector, while the other end is removably connected to the camera head 9 through a connector. Specifically, the transmission cable 8 is a cable in which multiple electrical wires (not illustrated) are arranged inside the inner part of an outer sheath that acts as the outermost layer. The multiple electrical wires are electrical wires for transmitting the imaging signal output from the camera head 9, as well as a control signal, a synchronization signal, a clock, and power output from the control device 5 to the camera head 9, respectively.

The display device 4, under control by the control device 5, displays an image generated by the control device 5. The display device 4 preferably includes a display of at least 55 inches to achieve a sense of immersion more easily during observation, but is not limited thereto.

The control device 5 processes the imaging signal input from the camera head 9 through the transmission cable 8, and outputs an image signal to the display device 4. In addition, the control device 5 also centrally controls the operations of the camera head 9 and the display device 4. Note that the detailed configuration of the control device 5 will be discussed later.

Figure 2:
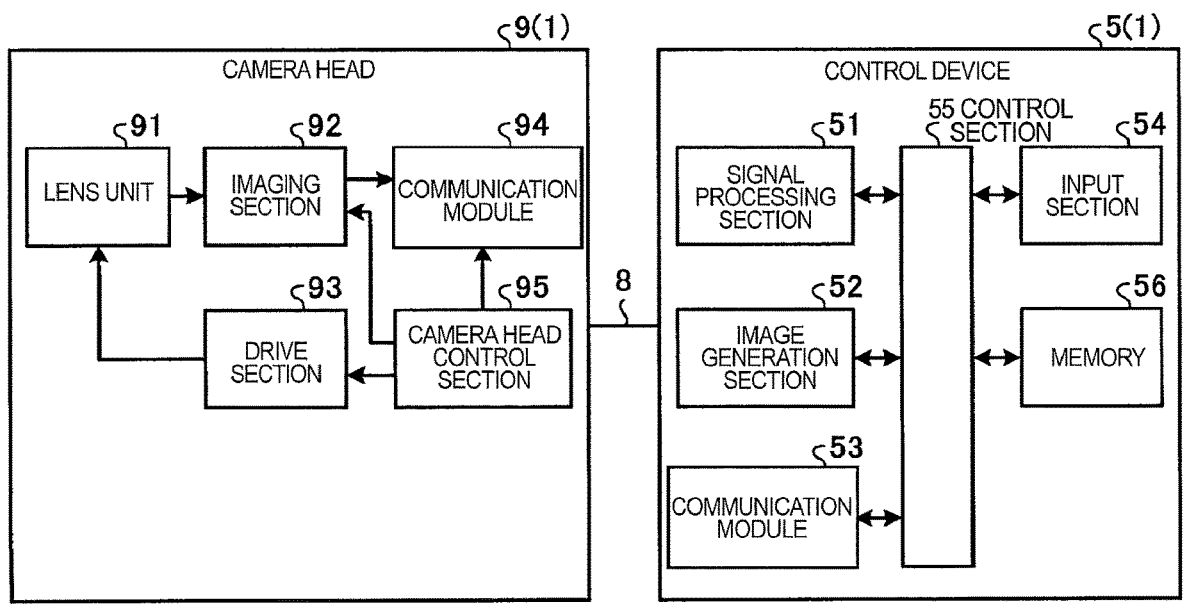
FIG. 2 is a block diagram illustrating a configuration of the camera head and the control device illustrated in FIG. 1.

Next, a configuration of the imaging device 3 and the control device 5 will be described. FIG. 2 is a block diagram illustrating a configuration of the imaging device 3 and the control device 5. Note that in FIG. 2, the connector that allows the camera head 9 and the transmission cable 8 to be removably connected to each other is omitted from illustration.

Hereinafter, the configuration of the control device 5 and the configuration of the camera head 9 will be described in order. Note that in the following, the gist of the present disclosure is described primarily as the configuration of the control device 5. As illustrated in FIG. 2, the control device 5 is equipped with a signal processing section 51, an image generation section 52, a communication module 53, an input section 54, a control section 55, and memory 56. Note that the control device 5 may also be provided with components such as a power supply section (not illustrated) that generates a power supply voltage for driving the control device 5 and the camera head 9 and respectively supplies the power supply voltage to each component of the control device 5, while also supplying the power supply voltage to the camera head 9 through the transmission cable 8.

The signal processing section 51 performs signal processing such as noise removal, and if necessary, A/D conversion, on the imaging signal output by the camera head 9, and outputs a digitized imaging signal (pulse signal) to the image generation section 52.

Additionally, the signal processing section 51 generates a synchronization signal for the imaging device 3 and the control device 5, and a clock. The synchronization signal for the imaging device 3 (such as a synchronization signal indicating the imaging timings of the camera head 9, for example) and the clock (a clock used for serial communication, for example) are sent to the imaging device 3 on a line not illustrated, and the imaging device 3 drives on the basis of the synchronization signal and the clock.

The image generation section 52 generates a display image signal to be displayed by the display device 4, based on the imaging signal input from the signal processing section 51. The image generation section 52 executes certain signal processing on the imaging signal to generate a display image signal that includes the subject image. Herein, the image processing may be any of various types of image processing, such as interpolation processing, color correction processing, color enhancement processing, and edge enhancement processing. The image generation section 52 outputs the generated image signal to the display device 4.

The communication module 53 outputs, to the imaging device 3, a signal from the control device 5 including a control signal discussed later that is transmitted from the control section 55. The communication module 53 also outputs a signal from the imaging device 3 to the control device 5. In other words, the communication module 53 is a relay device that outputs the signals from the respective components of the control device 5 to the imaging device 3 in a collective manner, such as by parallel-serial conversion, for example, and also outputs a signal input from the imaging device 3 to the respective components of the control device 5 in a distributed manner, such as by serial-parallel conversion, for example.

The input section 54 is realized using a user interface such as a keyboard, a mouse, or a touch panel, and accepts the input of various information.

The control section 55 performs controls such as drive control of each component, including the control device 5 and the camera head 9, and input/output control of information with respect to each component. The control section 55 generates a control signal by referencing communication information data recorded in the memory 56 (such as communication format information, for example), and transmits the generated control signal to the imaging device 3 through the communication module 53. The control section 55 also outputs a control signal to the camera head 9 through the transmission cable 8.

The memory 56 is realized using semiconductor memory such as flash memory or dynamic random access memory (DRAM), and records communication information data (such as communication format information, for example). Note that the memory 56 may also record information such as various programs executed by the control section 55.

Note that the signal processing section 51 may also include an AF processing section that outputs a certain AF score value for each frame based on an input frame imaging signal, and an AF computation section that performs an AF computational process of selecting the frame or the focus lens position best suited as the focus position, based on the AF score value of each frame from the AF processing section.

Note that the signal processing section 51, the image generation section 52, the communication module 53, and the control section 55 discussed above are realized by a general-purpose processor such as a central processing unit (CPU) including internal memory (not illustrated) in which a program is recorded, or by a special-purpose processor such as any of various types of computational circuits that execute a specific function, such as an application-specific integrated circuit (ASIC). Additionally, a field-programmable gate array (FPGA; not illustrated), which is a type of programmable integrated circuit, may also be used to realize the above. Note that in the case of using an FPGA, memory storing configuration data may be provided, and the FPGA, that is, the programmable integrated circuit, may be configured according to configuration data read out from the memory.

Next, the gist of the present disclosure will be described primarily as the configuration of the camera head 9. As illustrated in FIG. 2, the camera head 9 is equipped with a lens unit 91, an imaging section 92, a drive section 93, a communication module 94, and a camera head control section 95.

The lens unit 91 is configured using one or multiple lenses, and forms a subject image condensed by the endoscope 2 onto the imaging surface of an image sensor constituting the imaging section 92. The one or multiple lenses are movably configured along the optical axis. Additionally, the lens unit 91 is provided with a focus mechanism that moves the one or multiple lenses to vary an optical zoom mechanism (not illustrated) that varies the angle of view, or the focus point. Note that, besides the optical zoom mechanism and the focus mechanism, the lens unit 91 may also be provided with a diaphragm mechanism, or an optical filter (for example, a filter that cuts infrared light) that may be freely inserted or removed from the optical axis.

The imaging section 92 images a subject, under control by the camera head control section 95. The imaging section 92 includes an image sensor made of a device such as a charge-coupled device (CCD) or a complementary metal-oxide-semiconductor (CMOS) that senses the light of a subject image formed by the lens unit 91, and converts the light into an electrical signal. In the CCD case, for example, a signal processing section (not illustrated) that performs signal processing (such as A/D conversion) on the electrical signal (analog signal) from the image sensor and outputs an imaging signal is implemented in a sensor chip or the like. In the CMOS case, for example, a signal processing section that performs signal processing (such as A/D conversion) on an (analog) electrical signal converted from light into an electrical signal and outputs an imaging signal is included in the image sensor.

Figure 3:
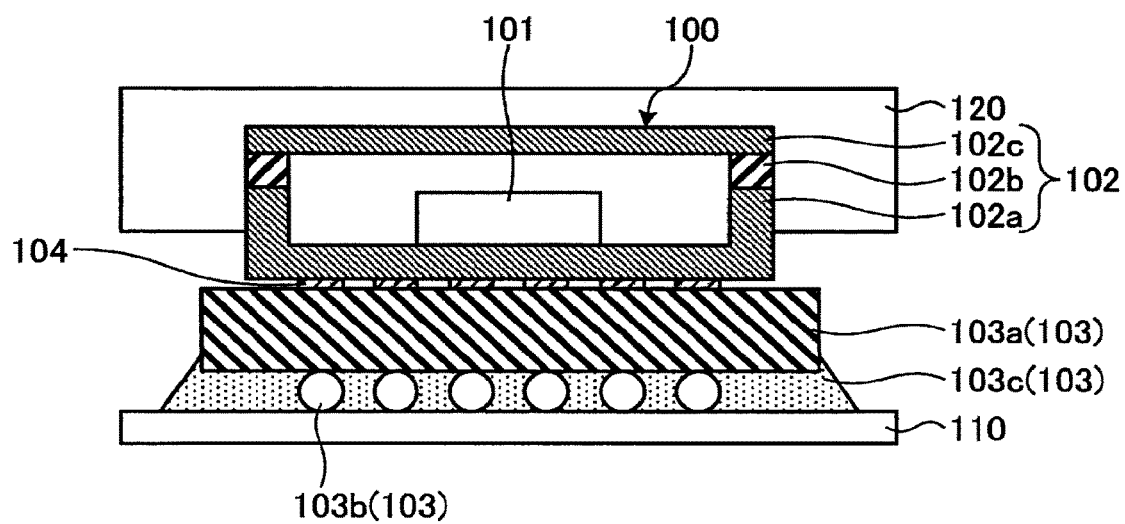
FIG. 3 is a schematic diagram explaining the major configuration of an imaging section according to Embodiment 1 of the present disclosure.

FIG. 3 is a schematic diagram explaining the major configuration of the imaging section 92. As illustrated in FIG. 3, the imaging section 92 includes an image sensor 101, a holding unit 102, an intermediate unit 103, a land grid array (LGA) 104, and a substrate 110. A lens adapter 120 is provided on the holding unit 102, and the imaging section 92 is attached to the lens unit 91 by the lens adapter 120. In the imaging section 92, observational light from outside the lens unit 91 is incident on the image sensor 101 through the lens unit 91. In Embodiment 1, the substrate 110 is taken to be formed using an organic material having a coefficient of thermal expansion from 12 ppm/° C. to 40 ppm/° C. in the direction along the mounting face at room temperature. In Embodiment 1, an image sensor section 100 is constituted by the image sensor 101 and the holding unit 102.

The image sensor 101 is realized using the CCD or CMOS discussed above. In the image sensor 101, multiple pixels that sense light from the lens unit 91 are arranged in a two-dimensional grid (arranged in a matrix). Additionally, the image sensor 101 generates an electrical signal (also called an image signal or the like) by performing photoelectric conversion on the light sensed by each of the pixels.

The image sensor 101 is electrically connected to the substrate 110, and includes a built-in circuit section that transmits and receives signals to and from the substrate 110.

The holding unit 102 forms a housing that holds the image sensor 101 inside. The holding unit 102 includes a holding section 102a, a ring section 102b, and a cap section 102c.

The holding section 102a forms a tube with a floor on one end, and holds the image sensor 101 in the floor section. The holding section 102a has a smaller coefficient of thermal expansion than the substrate 110, and is formed using a ceramic having a coefficient of thermal expansion from 4 ppm/° C. to 11 ppm/° C. in the direction along the mounting face at room temperature, for example.

The holding unit 102 forms a ring extending from open end of the holding section 102a. The ring section 102b is formed using a resin such as plastic, for example.

The cap section 102c has a plate-like shape, and is provided on the edge of the ring section 102b on the opposite side from the holding section 102a. With the cap section 102c, the opening in the floored tube formed by the holding section 102a and the ring section 102b is sealed. The cap section 102c is formed using an optically transparent material, such as glass, for example.

Note that in Embodiment 1, the image sensor section 100 is constituted by the image sensor 101 and the holding unit 102, but the configuration is not limited thereto, and the image sensor section 100 may also be constituted by the image sensor 101 only, for example.

The intermediate unit 103 is provided between the image sensor section 100 and the substrate 110. The intermediate unit 103 includes an intermediate member 103a, solder balls 103b, and underfill 103c.

The intermediate member 103a is provided internally with electrical interconnects, enabling an electrical connection between the image sensor 101 and the substrate 110. The intermediate member 103a may be a circuit board using a material such as ceramic, silicon, glass, or glass fiber reinforced epoxy resin as a substrate, for example, but is not limited thereto. The intermediate member 103a is formed using a material having the same coefficient of thermal expansion as the image sensor section 100, or a material having a coefficient of thermal expansion that is close to the image sensor section 100 from between the image sensor section 100 and the substrate 110. Specifically, the intermediate member 103a is formed using a material having a coefficient of thermal expansion whose value is 95% or greater than the coefficient of thermal expansion of the holding section 102a, and also less than or equal to an intermediate value between the coefficient of thermal expansion of the holding section 102a and the coefficient of thermal expansion of the substrate 110.

The solder balls 103b are provided between the intermediate member 103a and the substrate 110. The solder balls 103b transmit signals from the substrate 110 to the intermediate member 103a, and also transmit signals from the intermediate member 103a to the substrate 110.

The underfill 103c surrounds the solder balls 103b and fills in the space between the intermediate member 103a and the substrate 110, and preferably fills in the space to cover the solder balls 103b without gaps, but is not limited thereto. The underfill 103c is a material with less elasticity than the intermediate member 103a and the substrate 110. The underfill 103c preferably is a material having a glass transition temperature of 120° C. or more, but is not limited thereto. The underfill 103c is formed using a material having a coefficient of thermal expansion from 30 ppm/° C. to 50 ppm/° C. at room temperature after hardening, for example. The underfill 103c fixes the intermediate member 103a and the substrate 110 in place, and in addition, by surrounding the solder balls 103b, reduces corrosion of the solder balls 103b. Note that the underfill 103c may also be formed using a material having a coefficient of thermal expansion with a value between the coefficient of thermal expansion of the intermediate member 103a and the coefficient of thermal expansion of the substrate 110.

The land grid array (LGA) 104 is realized using multiple flat electrode pads that electrically connect the image sensor section 100 and the intermediate unit 103.

The drive section 93 includes a driver that, under control by the camera head control section 95, causes the optical zoom mechanism and the focus mechanism to operate, and varies the angle of view and the focus position of the lens unit 91.

The communication module 94 outputs signals transmitted from the control device 5 to respective components inside the camera head 9, such as the camera head control section 95. Additionally, the communication module 94 converts information related to the current state of the camera head 9 and the like into a signal format according to a predetermined transmission scheme, and outputs the converted signal to the control device 5 through the transmission cable 8. In other words, the communication module 94 is a relay device that outputs a signal input from the control device 5 and the transmission cable 8 to respective components of the camera head 9 in a distributed manner, such as by serial-parallel conversion, for example, and also outputs signals from the respective components of the camera head 9 to the control device 5 and the transmission cable 8 in a collective manner, such as by parallel-serial conversion, for example.

The camera head control section 95 controls the operation of the camera head 9 overall, according to signals such as a drive signal input through the transmission cable 8, or an instruction signal output from an operating section by a user operation on the operating section, such as a switch provided exposed on the outer face of the camera head 9. Additionally, the camera head control section 95 outputs information related to the current state of the camera head 9 to the control device 5 through the transmission cable 8.

Note that the drive section 93, the communication module 94, and the camera head control section 95 discussed above are realized by a general-purpose processor such as a central processing unit (CPU) including internal memory (not illustrated) in which a program is recorded, or by a special-purpose processor such as any of various types of computational circuits that execute a specific function, such as an application-specific integrated circuit (ASIC). Additionally, an FPGA, which is a type of programmable integrated circuit, may also be used to realize the above. Note that in the case of using an FPGA, memory storing configuration data may be provided, and the FPGA, that is, the programmable integrated circuit, may be configured according to configuration data read out from the memory.

Note that the camera head 9 or the transmission cable 8 may also include a signal processing section that performs signal processing on an imaging signal generated by the communication module 94 or the imaging section 92. Additionally, based on a reference clock generated by an oscillator (not illustrated) provided inside the camera head 9, an imaging clock for driving the imaging section 92 and a driving clock for driving the drive section 93 may be generated and output to the imaging section 92 and the drive section 93, respectively. Furthermore, based on a synchronization signal input from the control device 5 through the transmission cable 8, timing signals for various processes in the imaging section 92, the drive section 93, and the camera head control section 95 may be generated and output to the imaging section 92, the drive section 93, and the camera head control section 95, respectively. Also, the camera head control section 95 may be provided not in the camera head 9, but instead in the transmission cable 8 or the control device 5.

In the endoscopic device 1 having the configuration described above, since the intermediate unit 103 is provided between the image sensor section 100 (holding section 102a) and the substrate 110, when exposed to high temperature (for example, 120° C.) by a sterilization process, such as with an autoclave, the stress due to deformation of the substrate 110 by thermal expansion (thermal strain) is kept from spreading from the substrate 110 to the holding section 102a. Specifically, the stress due to the thermal expansion of the substrate 110 spreads to the underfill 103c of the intermediate unit 103, but is absorbed by deformation of the underfill 103c. Moreover, since the coefficient of thermal expansion of the intermediate member 103a is the same or close to that of the holding section 102a, little to no stress is transmitted to the holding section 102a side. For this reason, the holding section 102a is able to make a reliable electrical connection between the substrate 110 and the image sensor 101, without the connection to the intermediate member 103a (the joined state provided by the LGA 104) being broken by stress arising in the substrate 110. Likewise, deformation due to thermal expansion of the image sensor section 100 (holding section 102a) similarly is kept from spreading to the substrate 110. In contrast, in JP 2011-000346A, this thermal expansion is not considered, and stress from the substrate (drive circuit board) is imparted to the joint interface with the spacer and the image sensor, thereby producing a faulty electrical connection with the image sensor.

According to Embodiment 1 discussed above, the intermediate unit 103 is provided between the holding unit 102 that holds the image sensor 101, and the substrate 110, and the intermediate member 103a included in the intermediate unit 103 is formed with a material having approximately the same coefficient of thermal expansion as the holding section 102a of the holding unit 102. Consequently, even when exposed to high temperature (for example, 120° C.) by a sterilization process, such as with an autoclave, the stress due to deformation of the substrate 110 by thermal expansion is kept from spreading from the substrate 110 to the holding section 102a. Thus, a reliable electrical connection may be made between the image sensor 101 and the substrate 110, even when exposed to high temperature.

In addition, according to Embodiment 1 above, since the connection structure between the holding unit 102 and the intermediate unit 103 is an LGA structure, the gap between the holding unit 102 and the intermediate unit 103 may be reduced, and the configuration of the imaging section 92 may be made thinner.

Additionally, according to Embodiment 1 above, since the electrical connection between the intermediate member 103a and the substrate 110 is made with a ball grid array (BGA) structure using the solder balls 103b, compared to the case of using an LGA structure, for example, the gap between the intermediate member 103a and the substrate 110 may be increased, thereby increasing the volume in which the underfill 103c is used, and making it possible to improve workability related to the filling of the underfill 103c and the like, while also obtaining even more reliably the stress-absorbing advantages provided by the underfill 103c. For example, when using the solder balls 103b, the distance between the intermediate member 103a and the substrate 110 is 400 µm, whereas when using an LGA structure, the distance between the intermediate member 103a and the substrate 110 is approximately 40 µm.

Also, according to Embodiment 1 above, since the intermediate member 103a is provided between the image sensor section 100 and the substrate 110, compared to the case of directly joining the image sensor section 100 and the substrate 110, the interval between the image sensor section 100 and the substrate 110 becomes larger, and the workability related to the assembly of the imaging section 92 may be improved. A lens adapter 120 larger than the image sensor section 100 sometimes is affixed to the image sensor section 100 with a thermosetting resin or the like, and the view between the image sensor section 100 and the substrate 110 may become narrow in some cases, but by providing the intermediate member 103a, the interval between the image sensor section 100 and the substrate 110 is increased, thereby ensuring the view and improving workability.

(Modification 1 of Embodiment 1)

Figure 4:
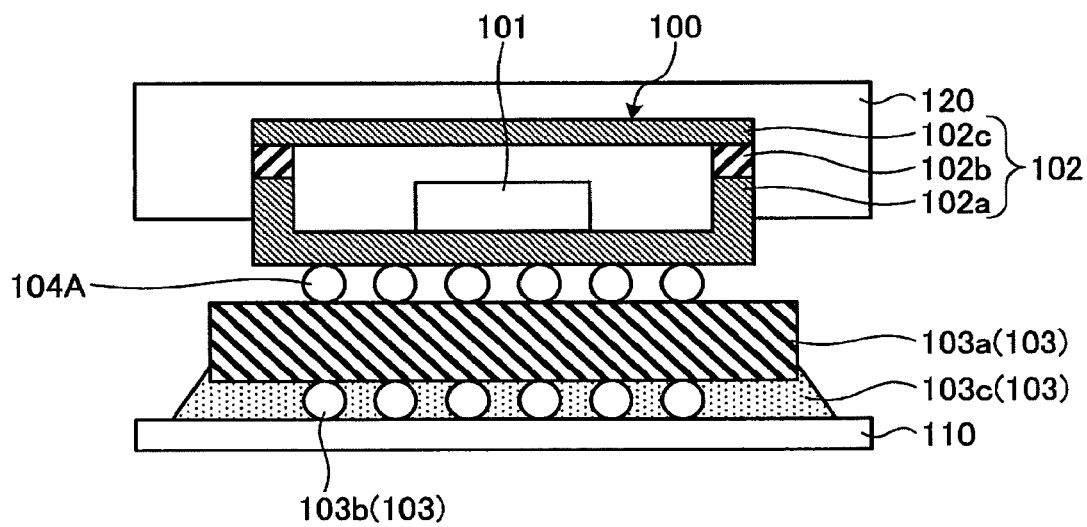
FIG. 4 is a schematic diagram explaining the major configuration of an imaging section according to Modification 1 of Embodiment 1 of the present disclosure.

Next, Modification 1 of Embodiment 1 of the present disclosure will be described. FIG. 4 is a schematic diagram explaining the major configuration of an imaging section according to Modification 1 of Embodiment 1 of the present disclosure. In Embodiment 1 above, the holding section 102a and the intermediate unit 103 are described as being connected electrically by the LGA 104, but in this modification, the holding section 102a and the intermediate unit 103 are connected electrically by solder balls.

In this modification, the configuration of the imaging section 92 discussed earlier is provided with a ball grid array (BGA) 104A instead of the LGA 104. The BGA 104A is realized using multiple globular electrodes (solder balls) that electrically connect the holding unit 102 and the intermediate unit 103.

Note that the solder balls used for the BGA 104A and the solder balls 103b discussed earlier may be made of solder only, but may also be solder balls including a different material, such as copper-core solder balls, in which copper is provided in the core, or resin-core solder balls, in which resin is provided in the core, for example. Note that to decrease faulty electrical connections due to a difference in the coefficient of thermal expansion between the image sensor section 100 (holding section 102a) and the substrate 110, it is preferable to use resin-core solder balls for the BGA 104A and/or the solder balls 103b.

Additionally, underfill similar to the underfill 103c of the intermediate unit 103 may also be used to fill in the BGA 104A, or in other words, the space between the image sensor section 100 and the intermediate unit 103.

According to Modification 1, similarly to Embodiment 1 discussed above, the intermediate unit 103 is provided between the holding unit 102 that holds the image sensor 101, and the substrate 110, and the intermediate member 103a included in the intermediate unit 103 is formed with a material having approximately the same coefficient of thermal expansion as the holding section 102a of the holding unit 102. Consequently, even when exposed to high temperature (for example, 120° C.) by a sterilization process, such as with an autoclave, the stress due to deformation of the substrate 110 by thermal expansion is kept from spreading from the substrate 110 to the holding section 102a. Thus, a reliable electrical connection may be made between the image sensor 101 and the substrate 110, even when exposed to high temperature.

Additionally, according to Modification 1, since the BGA 104A is provided between the image sensor section 100 and the substrate 110, the gap between the image sensor section 100 and the substrate 110 becomes even larger compared to the LGA 104, and the workability related to the assembly of the imaging section 92 may be improved.

(Modification 2 of Embodiment 1)

Figure 5:
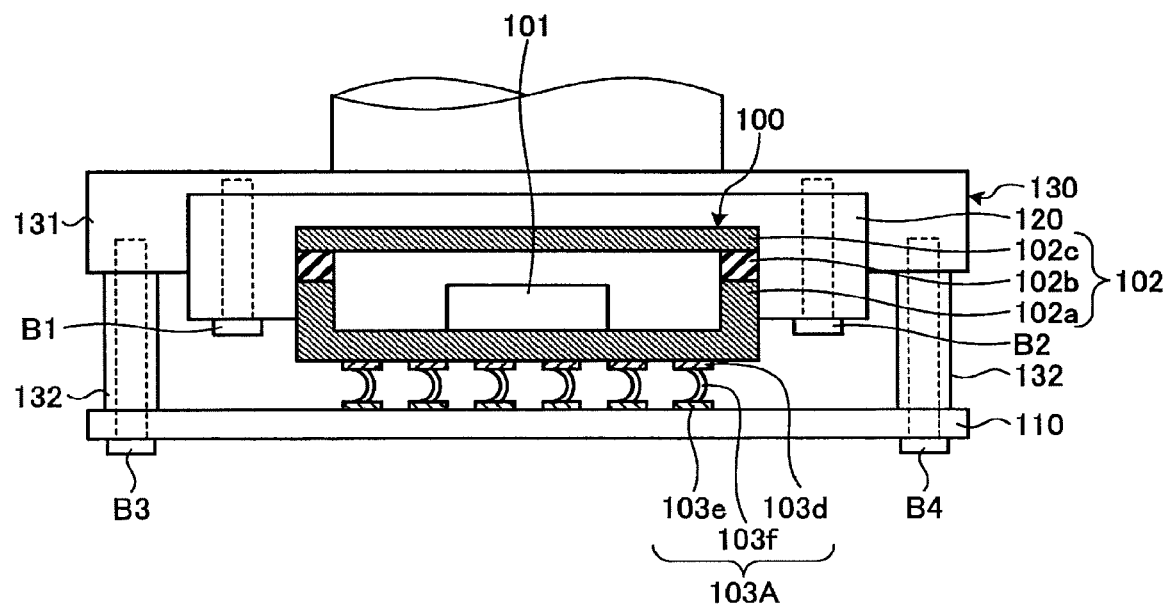
FIG. 5 is a schematic diagram explaining the major configuration of an imaging section according to Modification 2 of Embodiment 1 of the present disclosure.

Next, Modification 2 of Embodiment 1 of the present disclosure will be described. FIG. 5 is a schematic diagram explaining the major configuration of an imaging unit according to Modification 2 of Embodiment 1 of the present disclosure. In Embodiment 1 above, the intermediate unit 103 is described as including the intermediate member 103a, the solder balls 103b, and the underfill 103c, and is described as electrically connecting the image sensor section 100 and the substrate 110 with the intermediate member 103a and the solder balls 103b, while also using the underfill 103c to keep stress from the substrate 110 from being transmitted to the image sensor section 100. However, in Modification 2, an elastic member 103f is used to electrically connect the image sensor section 100 and the substrate 110 as well as keep stress from the substrate 110 from being transmitted to the image sensor section 100.

In Modification 2, the configuration of the imaging section 92 discussed earlier is provided with an intermediate unit 103A instead of the intermediate unit 103 and the LGA 104, and also is provided with a holding unit 130 that holds the lens unit 91 while also supporting the lens adapter 120 and the substrate 110. The lens adapter 120 is attached to the holding unit 130 by screws B1 and B2.

The intermediate unit 103A includes first electrode pads 103d that electrically connect to the image sensor section 100, specifically the circuit (electrodes) of the holding section 102a, second electrode pads 103e that electrically connect to the circuit (electrodes) of the substrate 110, and an elastic member 103f allowing electrical connection between the first electrode pads 103d and the second electrode pads 103e, while also being elastically deformable. The elastic member 103f is formed using a conductive material, such as a conductive metal or alloy, for example, and is formed by curving a belt-shaped member. Note that the elastic member 103f is not limited to the above insofar as the elastic member 103f is conductive and elastic, and may also be a conductive coil spring, for example.

The holding unit 130 holds the lens unit 91, and includes a holding section 131 that holds the lens adapter 120 via screws B1 and B2, and multiple support members 132 provided between the holding section 131 and the substrate 110 that support the substrate 110 with respect to the holding unit 130. The support members 132 are attached to the substrate 110 by screws B3 and B4.

In the endoscopic device having the configuration described above, since the intermediate unit 103A including the conductive elastic member 103f is provided between the holding unit 102 that holds the image sensor 101 and the substrate 110, when exposed to high temperature (for example, 120° C.) by a sterilization process, such as with an autoclave, the stress due to deformation of the substrate 110 by thermal expansion is kept from spreading from the substrate 110 to the holding section 102a. Specifically, the stress produced by the thermal expansion of the substrate 110 is absorbed by elastic deformation of the elastic member 103f of the intermediate unit 103A, with little to no stress being transmitted to the holding section 102a side. For this reason, the holding section 102a is able to make a reliable electrical connection between the substrate 110 and the image sensor 101, without the connection to the intermediate unit 103A being broken by stress from the substrate 110.

According to Modification 2, the elastic member 103f having conductive and elastic properties is provided between the holding unit 102 that holds the image sensor 101, and the substrate 110, thereby electrically connecting the image sensor section 100 and the substrate 110 while also keeping stress from the substrate 110 from being transmitted to the image sensor section 100. Thus, a reliable electrical connection between the image sensor 101 and the substrate 110 may be made, even when exposed to high temperature.

(Modification 3 of Embodiment 1)

Figure 6:
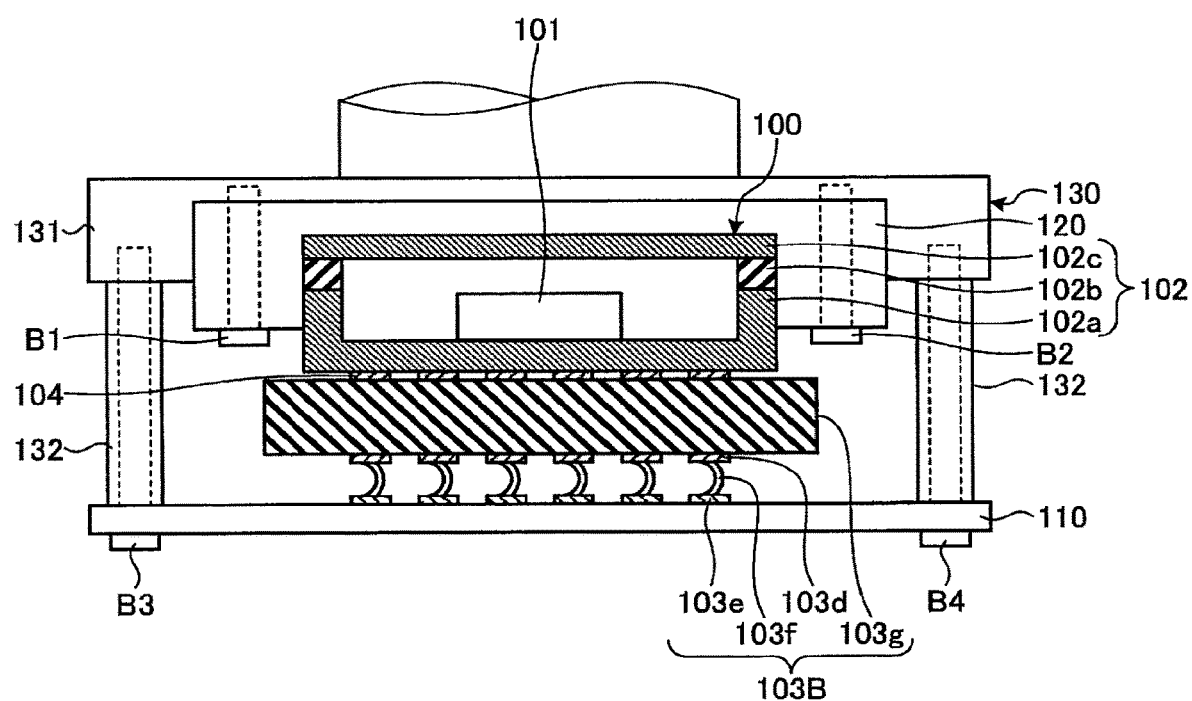
FIG. 6 is a schematic diagram explaining the major configuration of an imaging section according to Modification 3 of Embodiment 1 of the present disclosure.

Next, Modification 3 of Embodiment 1 of the present disclosure will be described. FIG. 6 is a schematic diagram explaining the major configuration of an imaging unit according to Modification 3 of Embodiment 1 of the present disclosure. In Modification 2 above, the intermediate unit 103A is described as including the first electrode pads 103d, the second electrode pads 103e, and the elastic member 103f, but in Modification 2, an intermediate member 103g is provided in addition to the configuration of the intermediate unit 103A.

In Modification 3, the configuration of the imaging section 92 discussed earlier is provided with an intermediate unit 103B instead of the intermediate unit 103A. The intermediate unit 103B includes the first electrode pads 103d, the second electrode pads 103e, and the elastic member 103f discussed above, as well as an intermediate member 103g.

The intermediate member 103g, similarly to the intermediate member 103a discussed earlier, is provided internally with electrical interconnects, enabling an electrical connection between the image sensor 101 and the substrate 110. The intermediate member 103g is formed using a material having a glass transition temperature of 120° C. or more, and the same coefficient of thermal expansion as the image sensor section 100, or a coefficient of thermal expansion that is close to the image sensor section 100 from between the image sensor section 100 and the substrate 110. Specifically, the intermediate member 103g is formed using a material having a coefficient of thermal expansion whose value is 95% or greater than the coefficient of thermal expansion of the holding section 102a, and also less than or equal to an intermediate value between the coefficient of thermal expansion of the holding section 102a and the coefficient of thermal expansion of the substrate 110.

The holding unit 130 holds the lens unit 91, and includes a holding section 131 that holds the lens adapter 120 via screws B1 and B2, and multiple support members 132 provided between the holding section 131 and the substrate 110 that support the substrate 110 with respect to the holding unit 130. The support members 132 are attached to the substrate 110 by screws B3 and B4.

In the endoscopic device having the configuration described above, since the intermediate unit 103B including the conductive elastic member 103f is provided between the holding unit 102 that holds the image sensor 101 and the substrate 110, when exposed to high temperature (for example, 120° C.) by a sterilization process, such as with an autoclave, the stress due to deformation of the substrate 110 by thermal expansion is kept from spreading from the substrate 110 to the holding section 102a. Specifically, the stress produced by the thermal expansion of the substrate 110 is absorbed by elastic deformation of the elastic member 103f of the intermediate unit 103B, with little to no stress being transmitted to the holding section 102a side. For this reason, the holding section 102a is able to make a reliable electrical connection between the substrate 110 and the image sensor 101, without the connection to the intermediate unit 103B (the joined state provided by the LGA 104) being broken by stress from the substrate 110.

According to Modification 3, the elastic member 103f having conductive and elastic properties is provided between the holding unit 102 that holds the image sensor 101, and the substrate 110, thereby electrically connecting the image sensor section 100 and the substrate 110 while also keeping stress from the substrate 110 from being transmitted to the image sensor section 100. Thus, a reliable electrical connection between the image sensor 101 and the substrate 110 may be made, even when exposed to high temperature.

(Embodiment 2)

Figure 7:
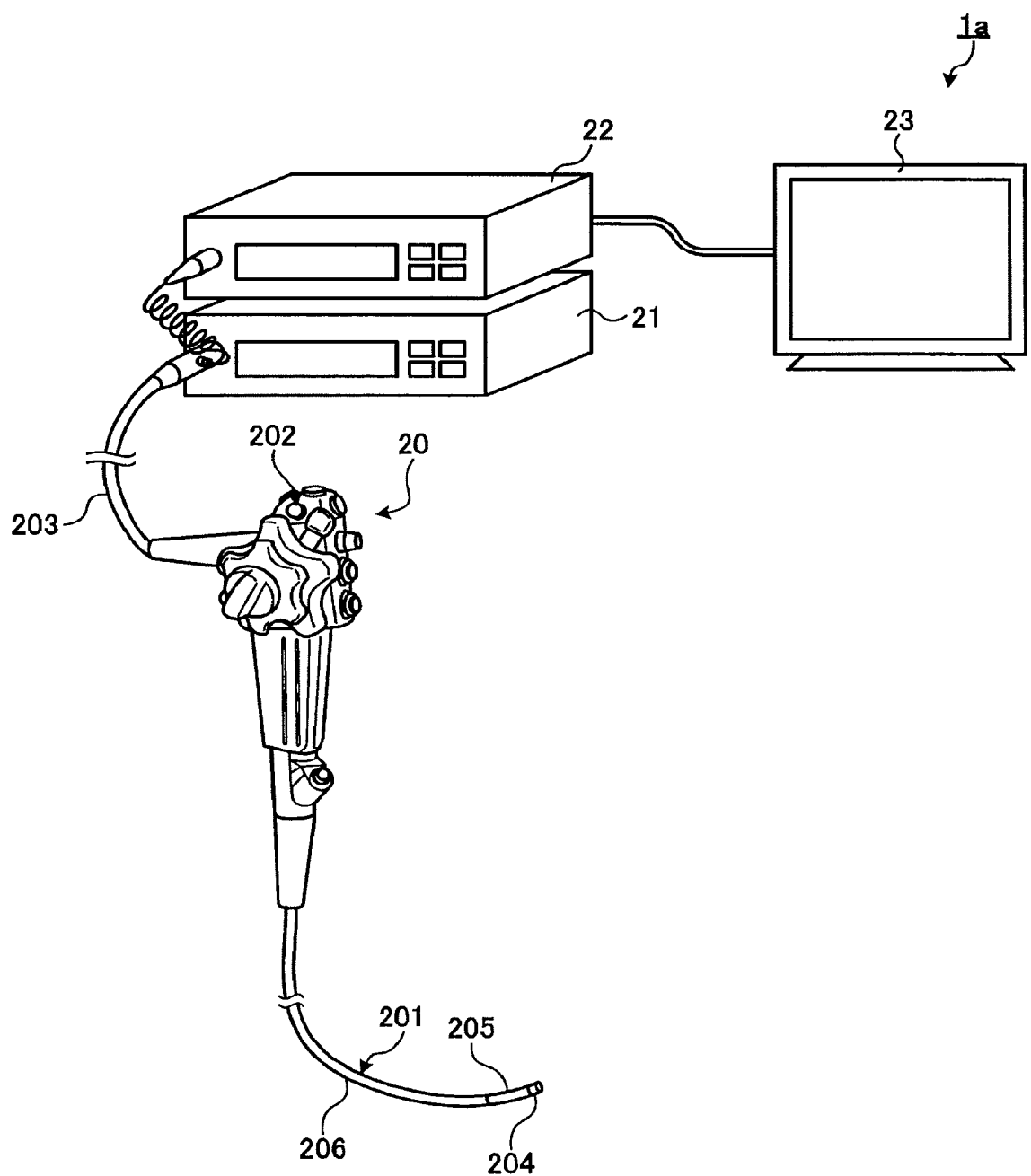
FIG. 7 is a diagram illustrating a schematic configuration of an endoscopic device according to Embodiment 2 of the present disclosure.

Next, Embodiment 2 of the present disclosure will be described. FIG. 7 is a diagram illustrating a schematic configuration of an endoscopic device 1a according to Embodiment 2 of the present disclosure. Embodiment 1 above describes an endoscopic device 1 using a rigid scope as the endoscope 2, but the configuration is not limited thereto, and an endoscopic device using a flexible scope as the endoscope 2 is also acceptable. Embodiment 2 describes an example of a case in which an imaging section is provided on the leading end of the insertion section of a flexible endoscope.

The endoscopic device 1a is equipped with an endoscope 20 that, by inserting an insertion section 201 inside a test subject's body, captures an internal image of an observation site and generates an electrical signal, a light source device 21 that produces illuminating light that radiates from the leading end of the endoscope 20, a control device 22 that performs certain image processing on the electrical signal acquired by the endoscope 20 and also centrally controls the operations of the endoscopic device 1a as a whole, and a display device 23 that displays an internal image processed by the control device 22. The endoscopic device 1a inserts the insertion section 201 inside the body of a test subject, such as a patient, and acquires an internal image of the inside of the test subject's body.

The endoscope 20 is equipped with a flexible insertion section 201 having a long and narrow shape, an operating section 202, connected to the base end side of the insertion section 201, that accepts the input of various operation signals, and a universal cord 203 which extends from the operating section 202 in a different direction from the direction in which the insertion section 201 extends, and which houses various cables that connect to the light source device 21 and the control device 22.

The insertion section 201 includes a leading end section 204 that houses the imaging section 92 according to Embodiment 1 discussed earlier, a freely bendable curved section 205 made up of multiple curve joints, and a flexible tube section 206 connected to the base end side of the curved section 205 and having a flexible elongated shape.

Likewise in the endoscopic device 1*a* having the above configuration, and similarly to the endoscopic device 1 discussed earlier, if the imaging section 92 is provided in the leading end section 204, even when exposed to high temperature (for example, 120° C.) by a sterilization process, such as with an autoclave, the stress due to deformation of the substrate 110 by thermal expansion is kept from spreading from the substrate 110 to the holding section 102*a*. Thus, a reliable electrical connection may be made between the image sensor 101 and the substrate 110, even when exposed to high temperature.

(Embodiment 3)

Next, Embodiment 3 of the present disclosure will be described. In Embodiment 1, the exchange of electrical signals, the supply of power, the connection to ground, and the like between the camera head 9 and the control device 5 are conducted by multiple electrical interconnects provided in the transmission cable 8, but in Embodiment 3, an optical signal is used for at least some signals transmitted and received between the camera head 9 and the control device 5, such as an imaging signal transmitted from the camera head 9 to the control device 5, for example.

Figure 8:
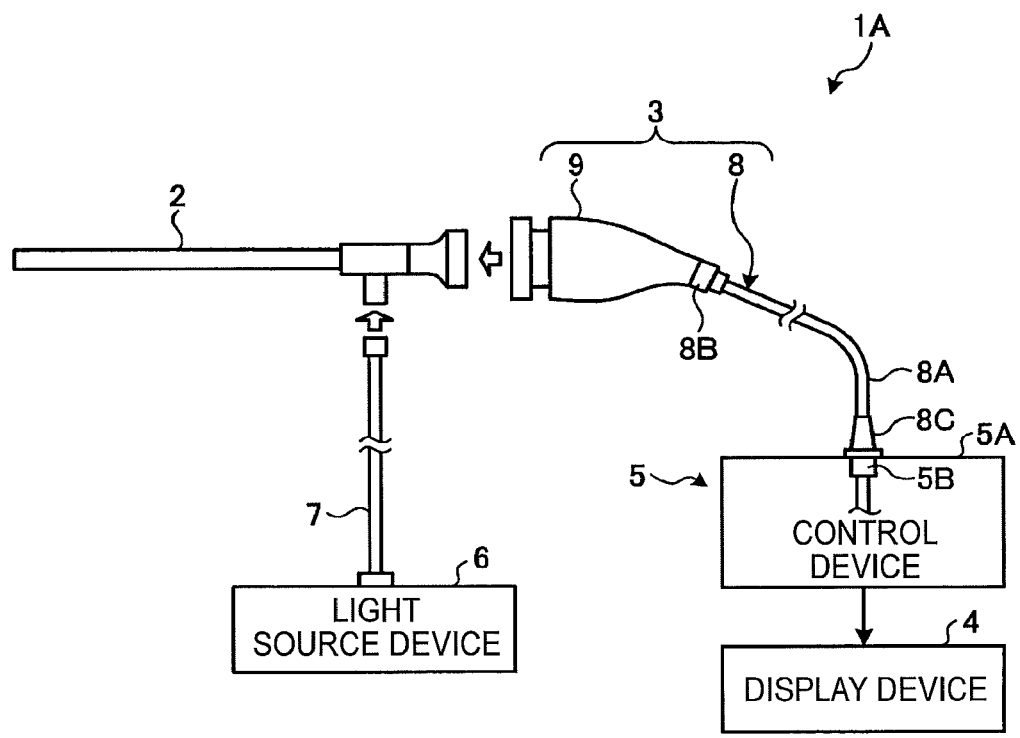
FIG. 8 is a diagram illustrating a schematic configuration of an endoscopic device according to Embodiment 2 of the present disclosure.
Figure 9:
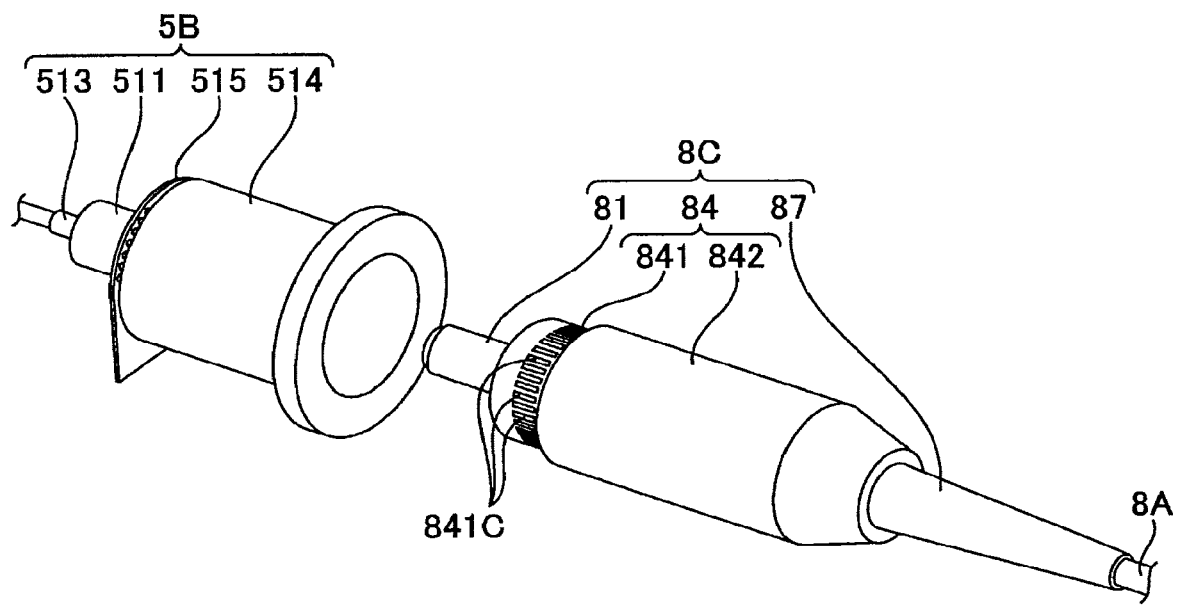
FIG. 9 is an exploded perspective diagram of a plug and a receptacle as viewed from base end side (camera head side) of the plug.
Figure 10:
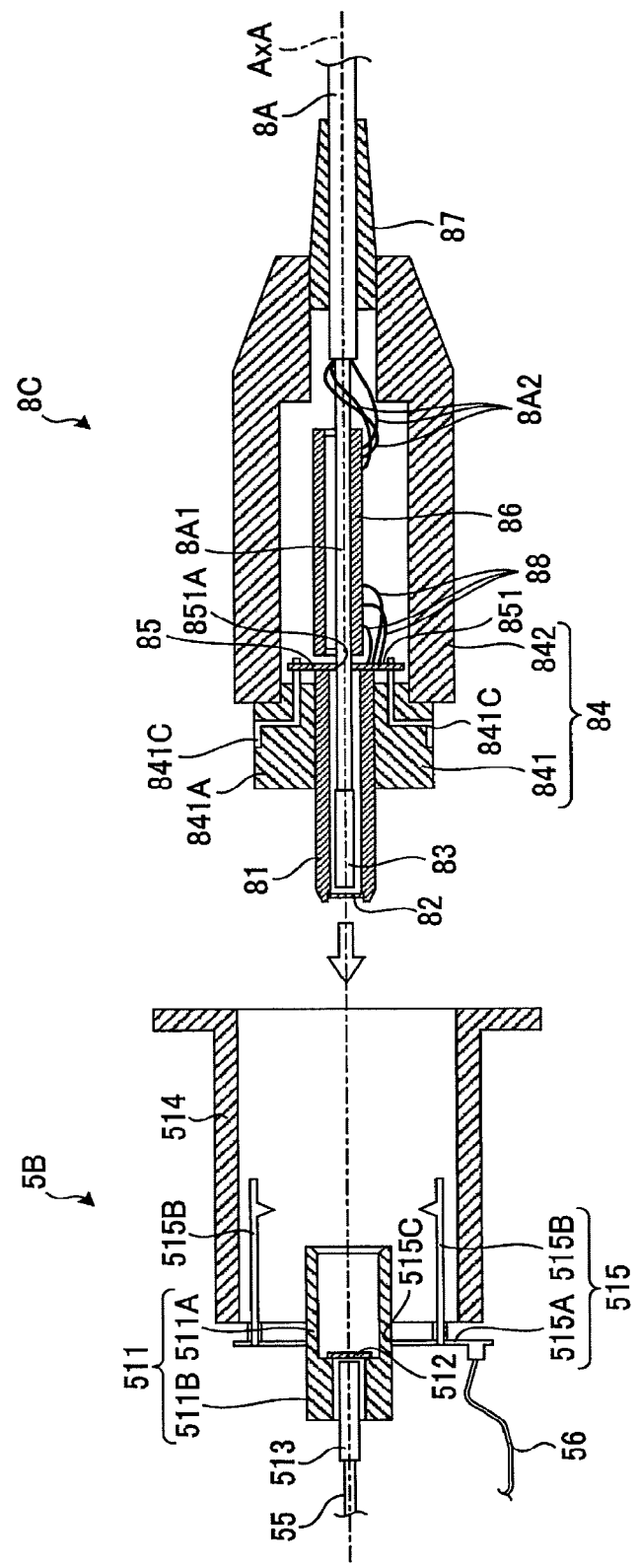
FIG. 10 is a cross-section view cut along a plane passing through a central axis in the direction in which a plug and a receptacle connect.

FIG. 8 is a diagram illustrating a schematic configuration of an endoscopic device 1A according to Embodiment 3 of the present disclosure. FIG. 9 is an exploded perspective view of a plug 8C and a receptacle 5B to be discussed later, as viewed from the base end side (camera head 9 side) of the plug 8C. FIG. 10 is a cross-section view cut along a plane passing through a central axis A×A in the direction in which the plug 8C and the receptacle 5B connect. Structural elements which are the same as structural elements discussed earlier will be denoted with the same signs. The endoscopic device 1A is equipped with an endoscope 2, an imaging device 3, a display device 4, a control device 5, and a light source device 6. The imaging device 3 is equipped with a transmission cable 8 and a camera head 9.

The transmission cable 8 is equipped with a cable section 8A, a connector 8B, and a plug 8C. The cable section 8A is a composite cable including, inside the inner part of an outer sheath (not illustrated) that acts as the outermost layer, an optical fiber 8A1, which is an optical transmission line that transmits optical signals such as imaging signals, for example, and multiple electrical cables 8A2, which are used to transmit and receive other electrical signals, supply power, connect to ground, and the like. Additionally, one end of the cable section 8A is connected to the camera head 9 through the connector 8B.

The plug 8C is a male connector, and corresponds to an optical connector according to an embodiment of the present disclosure. Additionally, the plug 8C is attached to the other end of the cable section 8A.

The receptacle 5B is a female connector provided on a housing 5A of the control device 5, and corresponds to an opposite connector.

By connecting the above plug 8C and the receptacle 5B to each other, the imaging device 3 and the control device 5 become connected both optically and electrically, thereby enabling the exchange of optical signals and electrical signals, the supply of power, and the connection to ground.

Next, the configuration of the plug 8C and the receptacle 5B will be described. The plug 8C is equipped with a plug-side first outer edge 81, a plug-side cover member 82, a plug-side collimator 83, a plug-side second outer edge 84, a connector section 85, a plug-side printed circuit board 86, and an elastic member 87.

As illustrated in FIGS. 9 and 10, the plug-side first outer edge 81 has an approximately cylindrical tube shape. Note that the plug-side first outer edge 81 is tubular, but is not limited to being cylindrical, and may also be configured as a tube having an elliptical, square, polygonal, or some other cross-sectional shape. Additionally, an optical fiber 8A1 constituting the cable section 8A is inserted through the plug-side first outer edge 81 inside the tube of the plug-side first outer edge 81, and the plug-side first outer edge 81 covers the light-emitting end of the optical fiber 8A1 from which an optical signal is emitted.

The plug-side cover member 82 is provided to cover the tube of the plug-side first outer edge 81, and is formed in a plate-like shape from a material that transmits light. The plug-side cover member 82 is joined airtight to the plug-side first outer edge 81 by soldering, brazing, or glass encapsulation. By sealing the leading end side of the plug-side first outer edge 81 with the plug-side cover member 82, the intrusion of liquid or foreign matter inside the plug-side first outer edge 81 may be restrained, and reliability of optical communication may be ensured.

The plug-side cover member 82 is positioned at a position retracted from the leading end of the plug-side first outer edge 81 toward the base end side of the plug-side first outer edge 81 (a position set back from the leading end). For this reason, the plug-side cover member 82 is structured to be less likely touched by hand, and the adhesion of foreign matter onto the plug-side cover member 82 may be restrained. In other words, the reliability of optical communication is not impaired by such foreign matter.

As illustrated in FIG. 10, the plug-side collimator 83 is disposed in a state joined to the light-emitting end of the optical fiber 8A1 inside the plug-side first outer edge 81. In other words, the plug-side collimator 83 is disposed between the plug-side cover member 82 and the light-emitting end of the optical fiber 8A1. Additionally, the plug-side collimator 83 collimates the light (optical signal) emitted from the light-emitting end of the optical fiber 8A1.

In the case of disposing the plug-side collimator 83, the mechanical connection with the receptacle 5B does not have to be as precise compared to a configuration that omits the plug-side collimator 83, thereby making fabrication of the plug 8C easier.

As illustrated in FIG. 10, the plug-side second outer edge 84 is equipped with a leading end side outer edge 841 and a base end side outer edge 842, and has an approximately cylindrical shape. Note that the plug-side second outer edge 84 is tubular, but is not limited to being cylindrical, and may also be configured as a tube having an elliptical, square, polygonal, or some other cross-sectional shape.

The leading end side outer edge 841 is provided with a base section 841A made from a non-conductive material, and multiple plug-side electrical contact points 841C made from a conductive material. As illustrated in FIG. 10, the plug-side electrical contact points 841C are provided partially exposed on the outer circumferential surface of the base section 841A. The multiple plug-side electrical contact points 841C are arranged at a certain interval in the circumferential direction of the leading end side outer edge 841.

In addition, the base end portion of the plug-side first outer edge 81 fits into the leading end side outer edge 841 so that the leading end portion of the plug-side first outer edge 81 projects outward. At this point, the space between the leading end side outer edge 841 and the plug-side first outer edge 81 is sealed with an O-ring, or with an adhesive sealant such as silicon resin or epoxy resin.

The base end side outer edge 842 is disposed on the base end side with respect to the leading end side outer edge 841. Additionally, the leading end portion of the base end side outer edge 842 fits against the base end side of the leading end side outer edge 841, with the cable section 8A internally inserted therethrough. At this point, the space between the base end side outer edge 842 and the leading end side outer edge 841 is sealed with an O-ring, or with an adhesive sealant such as silicon resin or epoxy resin.

As illustrated in FIG. 10, the connector section 85 is disposed inside the base end side outer edge 842, and bridges (electrically connects) the multiple plug-side electrical contact points 841C and the plug-side printed circuit board 86. The connector section 85 is equipped with a flat insulator 851 including a hole 851A through which the optical fiber 8A1 is inserted, and multiple contacts (not illustrated) made of conductive material that penetrate the insulator front-to-back. The multiple contacts electrically connect to each of the multiple plug-side electrical contact points 841C projecting out from the base end side of the leading end side outer edge 841, and also electrically connect to the plug-side printed circuit board 86, either directly or through connectors (not illustrated) and electrical interconnects 88.

As illustrated in FIG. 10, the plug-side printed circuit board 86 is disposed in a plane that includes the central axis A×A, and bridges the multiple plug-side electrical contact points 841C and the multiple electrical cables 8A2 that constitute the cable section 8A.

The elastic member 87 is a member that inhibits twisting of the cable section 8A around the inner edge perimeter of the base end portion of the base end side outer edge 842. Additionally, the leading end portion of the elastic member 87 fits into the base end portion of the base end side outer edge 842, with the cable section 8A internally inserted therethrough. At this point, the space between the elastic member 87 and the base end side outer edge 842 is sealed with an O-ring, or with an adhesive sealant such as silicon resin or epoxy resin.

As illustrated in FIG. 9 or 10, the receptacle 5B is equipped with a receptacle-side first outer edge 511, a receptacle-side cover member 512 (FIG. 10), a receptacle-side collimator 513, a receptacle-side second outer edge 514, and a receptacle-side printed circuit board 515.

The receptacle-side first outer edge 511 has a tubular shape in which are formed integrally a tubular large hole section 511A, which is positioned on the leading end side (the side that connects to the plug 8C), and a tubular small hole section 511B, which is positioned on the base end side and which has smaller inner hole dimensions that the inner hole dimensions of the large hole section 511A. Note that the receptacle-side first outer edge 511 is tubular, but is not limited to being cylindrical, and may also be configured as a tube having an elliptical, square, polygonal, or some other cross-sectional shape.

The large hole section 511A is formed so that the inner hole dimensions are slightly larger than the outer circumferential dimensions of the plug-side first outer edge 81. Additionally, the large hole section 511A is formed so that the lengthwise dimension (the dimension in the height direction of the tube) is slightly larger than the projection dimension from the plug-side second outer edge 84 (leading end side outer edge 841) on the plug-side first outer edge 81.

The receptacle-side cover member 512 is made of an optically transparent plate, placed against the step portion of the large hole section 511A and the small hole section 511B, and joined to the receptacle-side first outer edge 511. Note that the joining method may adopt the same joining method as the method of joining the plug-side cover member 82 to the plug-side first outer edge 81, or adopt a different joining method. Also, the receptacle-side cover member 512 may be made of the same material as the plug-side cover member 82, or may be made of a different material if the material has an optical transmittance by which optical communication may be established.

As illustrated in FIG. 10, the receptacle-side collimator 513 is inserted through the small hole section 511B. Additionally, the receptacle-side collimator 513 guides light (an optical signal) emitted from the plug-side collimator 83 to an internal circuit of the control device 5 through an optical fiber 55 (FIG. 10) that acts as an optical transmission line, for example.

In the case of disposing the receptacle-side collimator 513, the mechanical connection with the plug 8C does not have to be as precise compared to a configuration that omits the receptacle-side cover member 512, thereby making fabrication of the receptacle 5B easier.

The inner perimeter of the receptacle-side second outer edge 514 has a tubular shape allowing the insertion of the plug-side second outer edge 84. Additionally, the leading end portion of the receptacle-side first outer edge 511 is inserted into the receptacle-side second outer edge 514 so that the base end portion projects outward.

The receptacle-side printed circuit board 515 is equipped with a board body 515A and multiple receptacle-side electrical contacts 515B.

As illustrated in FIG. 10, the board body 515A includes a hole 515C that penetrates front-to-back in an approximate center portion. Additionally, the receptacle-side first outer edge 511 fits into the hole 515C.

The multiple receptacle-side electrical contacts 515B are made from a conductive material to electrically connect to the board body 515A, and also project into the tube of the receptacle-side second outer edge 514. The receptacle-side electrical contacts 515B are arranged at a certain interval in the circumferential direction of the receptacle-side first outer edge 511.

Additionally, the board body 515A bridges the multiple receptacle-side electrical contacts 515B and an internal circuit of the control device 5 through multiple electrical cables 56 (FIG. 10), for example.

In the state in which the plug 8C and the receptacle 5B discussed above are mechanically connected to each other, the plug-side first outer edge 81 is inserted into the receptacle-side first outer edge 511 (large hole section 511A). Additionally, in this state, the plug-side collimator 83 (the light-emitting end of the optical fiber 8A1) and the receptacle-side collimator 513 (the light-incident end of the optical fiber 55) face each other. In other words, this state is one in which an optical signal (imaging signal) output from the camera head 9 through the cable section 8A (optical fiber 8A1) is transmittable to an internal circuit of the control device 5 through the plug 8C and the receptacle 5B (a state enabling optical communication).

Additionally, in the state in which the plug 8C and the receptacle 5B are mechanically connected to each other, the plug-side second outer edge 84 is inserted into the receptacle-side second outer edge 514, and the multiple plug-side electrical contact points 841C are electrically connected to the multiple receptacle-side electrical contacts 515B, respectively. Additionally, in this state, controls signals, supplied power, and the like output from an internal circuit of the control device 5 are transmittable to the transmission cable 8 (camera head 9) through the receptacle 5B and the plug 8C.

Figure 11:
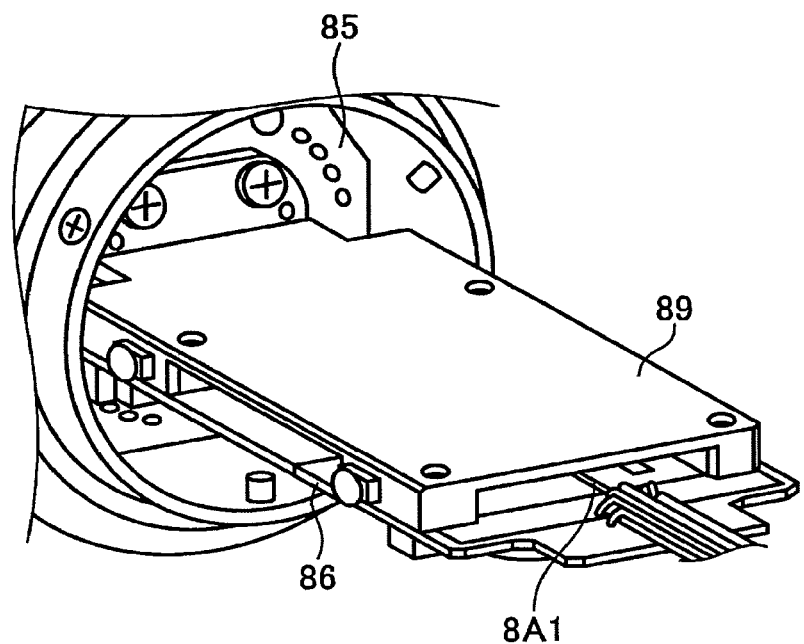
FIG. 11 is a diagram illustrating a major configuration of an endoscopic device according to Embodiment 3 of the present disclosure.
Figure 12:
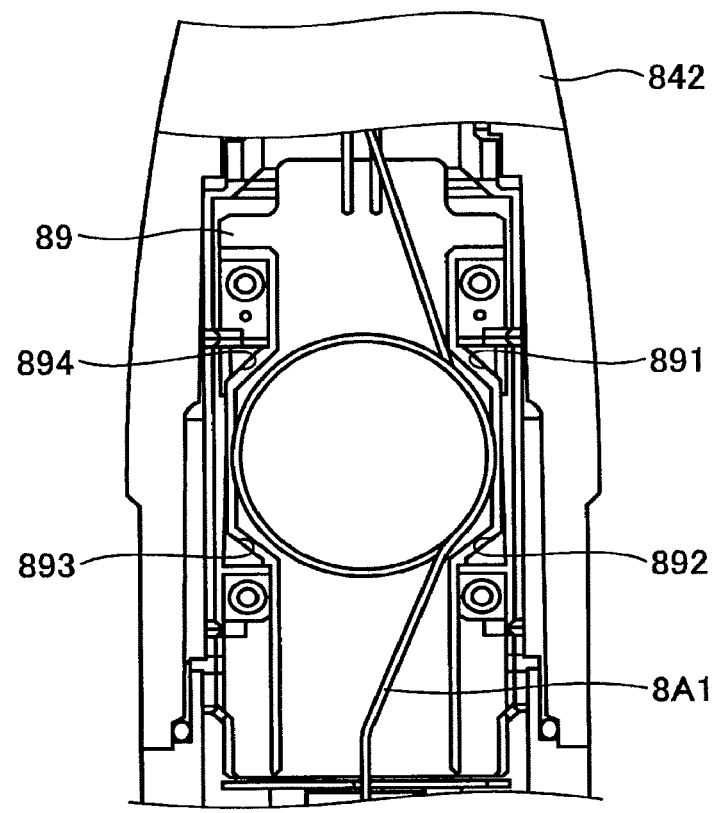
FIG. 12 is a diagram illustrating a major configuration of an endoscopic device according to Embodiment 3 of the present disclosure.

FIG. 11 is a diagram illustrating the major configuration of an endoscopic device according to Embodiment 3 of the present disclosure, and is an exploded perspective view illustrating the configuration of the plug 8C of the endoscopic device 1A illustrated in FIG. 8. FIG. 12 is a diagram illustrating the major configuration of an endoscopic device according to Embodiment 3 of the present disclosure, and is a partial cross-section view illustrating the configuration of the plug 8C of the endoscopic device 1A illustrated in FIG. 8. The cross-section view illustrated in FIG. 12 is a partial cross-section view taking a plane approximately parallel to the central axis A×A as the cross-section.

As illustrated in FIGS. 10 to 12, the plug 8C additionally includes a protective case 89 which is supported by the plug-side printed circuit board 86, and which protects the optical fiber 8A1 passing over the board. The optical fiber 8A1 is inserted through the hollow space formed by the faces of the protective case 89 and the plug-side printed circuit board 86 facing each other.

The protective case 89 is formed by press-working SUS, for example. The protective case 89 is screwed onto the plug-side printed circuit board 86, for example. By pressing and securing the protective case 89 onto the plug-side printed circuit board 86, the formation of a gap between the protective case 89 and the plug-side printed circuit board 86 is inhibited, thereby enabling the optical fiber 8A1 to be disposed without being caught in a gap formed between the protective case 89 and the plug-side printed circuit board 86. Note that the protective case 89 may be formed using a resin, such as polyphenylene sulfide (PPS), for example, may be formed by cutting metal, or may be formed with a composite material of resin and metal.

Additionally, as illustrated in FIG. 12, the optical fiber 8A1 is curved so as to draw a circle while being guided by the inner wall of the protective case 89, with any extra length of the optical fiber 8A1 wrapping around. This wraparound portion absorbs force in the extension direction of the optical fiber 8A1 when the transmission cable 8 is bent or twisted. Herein, the inner wall of the protective case 89 according to Embodiment 3 includes planar sections 891 to 894 extending in tangent directions to the direction by which the optical fiber 8A1 is wrapped around. Consequently, the optical fiber 8A1 may be wrapped around more stably.

According to Embodiment 3 discussed above, the protective case 89 that protects the optical fiber 8A1 passing over the plug-side printed circuit board 86 is including, thereby providing a configuration related to the protection of the optical fiber 8A1. In addition, the formation of a gap between the protective case 89 and the plug-side printed circuit board 86 is inhibited, the protective case 89 is easily fabricated, and the protective case 89 may be attached easily and reliably.

In addition, according to Embodiment 3, parts of the inner walls of the protective case 89 form planar sections 891 to 894 extending in tangent directions to the wraparound direction of the optical fiber 8A1. Consequently, when wrapping around extra length of the optical fiber 8A1 on the protective case 89, the optical fiber 8A1 may be wrapped around more smoothly and the shape of the wrap may be maintained better compared to a configuration in which the wall faces form corners.

The foregoing thus describes embodiment for carrying out the present disclosure, but the present disclosure should not be limited only to the embodiments discussed in the foregoing. In the foregoing embodiments, the control device 5 is described as conducting signal processing and the like, but such signal processing may also be conducted on the camera head 9 side.

Herein, in the foregoing Embodiments 1 and 2 as well as Modifications 1 to 3, the size of the image sensor section 100 used in the camera head 9 is from 8×6 (mm) to 50×40 (mm), for example, but the size of the image sensor section 100 provided in the leading end section 204 of the endoscopic device 1a is from 2×2 (mm) to 6×6 (mm), for example. The image sensor section 100 used in the camera head 9 is large compared to the size of the image sensor section in the endoscopic device 1a which is a flexible scope, and the deformation due to thermal expansion is large. For this reason, the configuration of the imaging section 92 according to the foregoing Embodiment 1 is considered to be particularly effective for the image sensor section 100 used in the camera head 9.

As above, a medical imaging device and endoscopic device according to an embodiment of the present disclosure is useful for making a reliable electrical connection between an image sensor and a substrate, even when exposed to high temperature.

It should be understood by those skilled in the art that various modifications, combinations, sub-combinations and alterations may occur depending on design requirements and other factors insofar as they are within the scope of the appended claims or the equivalents thereof.

What is claimed is:
1. An endoscopic device, comprising:
an image sensor configured to sense and convert light into one or more electrical signals;
a substrate that is electrically connected to the image sensor; and
an intermediate layer, interposed between the image sensor and the substrate, that electrically connects the image sensor and the substrate,
wherein the intermediate layer includes an intermediate member formed using a material having a first coefficient of thermal expansion whose value is 95% or greater than a second coefficient of thermal expansion of the image sensor, and also less than or equal to an intermediate value between the second coefficient of thermal expansion of the image sensor and a third coefficient of thermal expansion of the substrate
wherein the intermediate layer additionally includes
solder balls that electrically connect the intermediate member and the substrate, and
underfill, provided between the intermediate member and the substrate, that secures the intermediate member and the substrate, wherein the underfill is a material with less elasticity than the intermediate member and the substrate.

2. The endoscopic device according to claim 1, further comprising:
solder balls that electrically connect the image sensor and the intermediate member.

3. The endoscopic device according to claim 1, wherein the underfill formed using a material having a coefficient of thermal expansion with a value between the coefficient of thermal expansion of the intermediate member and the coefficient of thermal expansion of the substrate.

* * * * *